US010162415B2

(12) United States Patent
Richter et al.

(10) Patent No.: US 10,162,415 B2
(45) Date of Patent: Dec. 25, 2018

(54) SYSTEM IMPLANTABLE UNDER SKIN OF A LIVING ORGANISM

(71) Applicants: Wolfgang Richter, Vancouver (CA); Faranak Zadeh, Vancouver (CA)

(72) Inventors: Wolfgang Richter, Vancouver (CA); Faranak Zadeh, Vancouver (CA)

(73) Assignee: EPIC SEMICONDUCTORS INC, Vancouver British Columbia (CA)

( * ) Notice: Subject to any disclaimer, the term of this patent is extended or adjusted under 35 U.S.C. 154(b) by 191 days.

(21) Appl. No.: 15/377,866

(22) Filed: Dec. 13, 2016

(65) Prior Publication Data

US 2018/0164884 A1 Jun. 14, 2018

(51) Int. Cl.
*G06F 3/01* (2006.01)
*G08B 5/36* (2006.01)
(Continued)

(52) U.S. Cl.
CPC ............. *G06F 3/015* (2013.01); *A61N 1/205* (2013.01); *A61N 7/00* (2013.01); *G08B 5/36* (2013.01);
(Continued)

(58) Field of Classification Search
CPC ... G06F 3/015; G08B 5/36; A61N 2007/0017; A61N 7/00; A61N 1/205; H04B 7/24
See application file for complete search history.

(56) References Cited

U.S. PATENT DOCUMENTS

| 2003/0017804 A1* | 1/2003 | Heinrich | G06K 19/0701 |
| | | | 455/41.1 |
| 2006/0152209 A1* | 7/2006 | Sasaki | G01R 15/241 |
| | | | 324/96 |

(Continued)

*Primary Examiner* — Carolyn R Edwards

(57) ABSTRACT

Disclosed is a system for enhancing features of a living organism and further communicating the features with an external device. The system includes a flexible printed circuit implanted under the skin of a living organism and a host placed in proximity of the living organism for powering the flexible printed circuit implant wirelessly utilizing alternating charges. The living organism generates biological signals. The host further includes a memory unit connected to a controller for storing media data and operating instructions, a first electrode for emitting alternating charges with variable frequency, a second electrode floats against the ground; and an interface which wirelessly communicates with an external device. The flexible printed circuit includes a third electrode which mirrors said alternating charges received from the first electrode, and an energy convertor for changing the alternating charges to DC power. The flexible printed circuit includes a bi-directional communication unit to communicate signals with a modem for modulating and demodulating the generated modulated alternating frequency, and an analog I/O unit which processes biological signals received from the bi-directional communication unit. An electro-mechanic coupler enhances the biological signals, further the electro-mechanic coupler generates mechanical waves utilizing a fixed structure of said living organism. Further, the coupler converts mechanical waves into electrical signals and furthermore communicates the (Continued)

electrical signals containing processed biological signals with an analog I/O unit, and further the electro-mechanic coupler emits and receives alternating charges. Further, the analog I/O unit processes the electrical signals and communicates the information to the bi-directional communication unit.

12 Claims, 2 Drawing Sheets

(51) Int. Cl.
      *H04B 7/24*       (2006.01)
      *A61N 7/00*       (2006.01)
      *A61N 1/20*       (2006.01)

(52) U.S. Cl.
      CPC ........ H04B 7/24 (2013.01); *A61N 2007/0017* (2013.01)

(56) References Cited

U.S. PATENT DOCUMENTS

| | | | |
|---|---|---|---|
| 2012/0238899 A1* | 9/2012 | Bacquet | G06K 7/0008 600/549 |
| 2015/0347794 A1* | 12/2015 | Richter | G06K 19/0723 340/10.1 |
| 2016/0248481 A1* | 8/2016 | Richter | H02J 3/00 |

\* cited by examiner

SYSTEM IMPLANTABLE UNDER SKIN OF A LIVING ORGANISM

BACKGROUND OF THE INVENTION

Field of the Invention

The present invention generally relates to a system implantable under skin of a living organism, and more particularly relates to a system implantable under skin of living organisms for enhancing features and detecting gestures, and other body signals and communicating with an external device.

DESCRIPTION OF RELATED ART

Permanent body art is a growing cultural and social effect. People like to apply tattoos and piercings to their body as a sign of individuality, social engagement to groups or simply to alter their visual impression to others. Like fashion, such trends fade over time, so an improvement is needed. While extreme piercing is in progress, more and more people like the idea to have implants under the skin to create artfully "3D effects".

Another trend is to implement wearable computing devices or technologies into jewelry. As body piercing is a kind of jewelry, it is apparent that cosmetic implants will combine aesthetical and functional features. As the sense of jewelry is to gain attraction and get attention, dynamic effects have to replace simple aesthetical presence. Hence, it is likely that body implants will create such effects, e.g. illumination of body parts through the skin (dermis).

Therefore there is a need of a system that is self powered and is further implantable under the skin of living organism. The system should further enhance the senses of living organisms. Further, the system should be able to communicate sensing features, and other related data with external devices.

SUMMARY OF THE INVENTION

In accordance with teachings of the present invention, a system for enhancing features of a living organism and further communicating the features with an external device is provided.

An object of the present invention is to provide a system for enhancing features of a living organism. The system includes a flexible printed circuit implanted under the skin of a living organism and a host placed in proximity of the living organism for powering the flexible printed circuit implant. The living organism generates biological signals and is sensitive against mechanical waves.

The host includes a controller for generating commands, a generator for generating modulated alternating electric field with variable frequency, a modem for modulating and demodulating the generated modulated alternating frequency, and a first electrode for emitting alternating charges with variable frequency. The first electrode couples with the living organism.

The host further includes a memory unit connected to the controller for storing media data and operating instructions, a second electrode floating against the ground, and an interface which wirelessly communicates with the external device. The flexible printed circuit includes a third electrode which mirrors alternating charges received from the first electrode, and an energy convertor for changing the alternating charges to DC power.

The flexible printed circuit includes a bi-directional communication unit to communicate signals with the modem utilizing the alternating electric field and the biological signals, and an analog I/O unit which processes biological signals received from the bi-directional communication unit.

The flexible printed circuit further includes an electro-mechanic coupler coupled to a fixed structure of a living organism, further the electro-mechanic coupler enhances the biological signals, further the electro-mechanic coupler generates mechanical waves utilizing the fixed structure and further converts mechanical waves into electrical signals and furthermore communicates the electrical signals containing processed biological signals with the analog I/O unit, and further the electro-mechanic coupler emits and receives alternating charges.

Further, the analog I/O unit processes the electrical signals and communicates the information to the bi-directional communication unit, wherein the bi-directional unit communicates the information to the modem over the electric field, further wherein the controller processes signals from the modem and utilizing the memory unit for operating instructions and further the controller communicates the operating instructions and media data with the external device using the interface.

Another object of the present invention is to provide a system wherein the electro-mechanic coupler includes a mechanical acoustic coupler attached to the fixed structure of the living organism, a first conductive membrane attached to the mechanical acoustic coupler, a second conductive membrane connected to the first conductive membrane to emit an electric field over its surface.

Further, the second conductive membrane is coupled to the mechanical acoustic coupler. The mechanical acoustic coupler further includes a piezo material attached to the first conductive membrane and the second conductive membrane for generating mechanical waves.

The mechanical acoustic coupler combines the generated mechanical waves from the first conductive membrane and the second conductive membrane. Further the mechanical acoustic coupler filters high frequencies and conducts the resulting beat pattern to the fixed structure.

Further the electro-mechanical coupler includes a first piezo driver which operates the first conductive membrane and further receives power from the generator via the energy converter; and a second piezo driver which operates the second conductive membrane and further receives power from the generator via the energy converter.

The electro-mechanic coupler further includes a digital frequency modulator for modulating the frequency of the second membrane with the biological signal, and a biological signal modulator which receives biological signals from the second conductive membrane, furthermore the biological signal modulator modulates the biological signal into electric field received from the host.

Another object of the present invention is to provide the system wherein the flexible printed circuit implant further includes a light source for illuminating through the skin of the living organism on receiving commands from the controller. Further, the analog I/O unit stimulates nerve cells of the living organism on receiving commands from the controller.

Further, the analog I/O unit monitors nerve cells and further communicates the information to the controller through the bi-directional communication unit. Another object of the present invention is to provide the system wherein the host further includes a level shifter for creating controllable levels of modulated frequencies.

Further, the controller commands the light source unit to illuminate upon detecting specific biological signals from the living organism. Further, the light source unit is a multi-color LED, wherein the memory unit stores instructions for illuminating a specific color of the multi-color LED representing a specific biological signal. The controller commands the multi-color LED to illuminate the specific color corresponding to the specific biological signal.

Another object of the present invention is to provide the system wherein the flexible printed circuit releases electric fields and ultra sound waves to heal wounds or tissues of living organisms. The mechanical waves are either ultrasound waves or shocks or audible sounds or contraction of organic material of the living organisms.

DETAILED DESCRIPTION OF THE DRAWINGS

Figure 1:
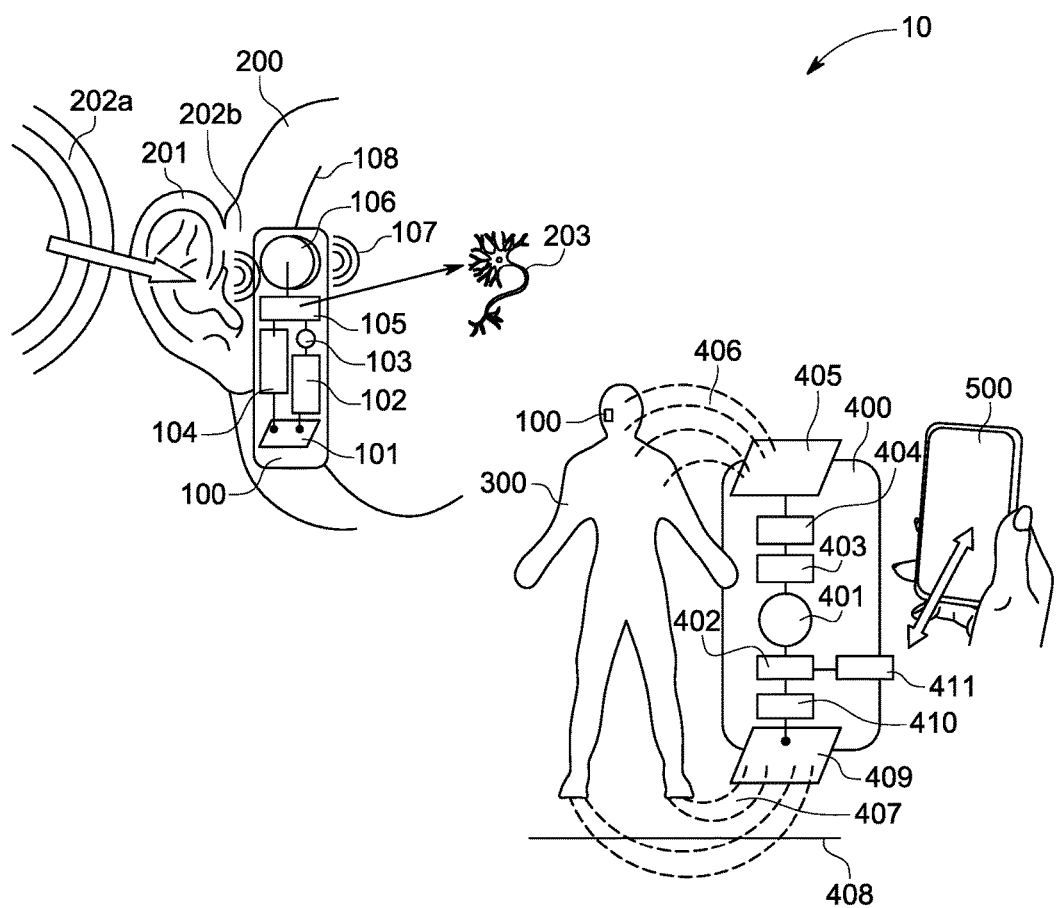
FIG. 1 illustrates a schematic diagram of a system for enhancing features of a living organism in accordance with a preferred embodiment of the present invention.

While this technology is illustrated and described in a preferred embodiment, a system for enhancing features of a living organism may be produced in many different configurations, shapes, sizes, forms and materials. There is depicted in the drawings, and will herein be described in detail, as a preferred embodiment of the invention, with the understanding that the present disclosure is to be considered as an exemplification of the principles of the invention and the associated functional specifications for its construction and is not intended to limit the invention to the embodiment illustrated. Those skilled in the art will envision many other possible variations within the scope of the technology described herein.

FIG. 1 illustrates a schematic diagram of a system 10 for enhancing features of a living organism 300 in accordance with a preferred embodiment of the present invention. The system 10 communicates the features with an external device 500. The system 10 includes a flexible printed circuit 100 implanted in skin of the living organism 300, and a host 400 placed in the proximity of the living organism 300 for powering the flexible printed circuit implant 100. The living organism 300 generates biological signals.

The host 400 includes a controller 402, a generator 401, a modem 403, a first electrode 405, a memory unit 410, a second electrode 409 and an interface 411. Further, the flexible printed circuit 100 includes a third electrode 101, an energy convertor 102, a bi-directional communication unit 104, an analog I/O unit 105, and an electro-mechanic coupler 106.

The controller 402 generates commands, the generator 401 generates a variable frequency, and the modem 403 modulates and demodulates the generated or modulated alternating frequency. The first electrode 405 emits alternating charges of the variable frequency. Further, the first electrode 405 couples with the living organism 300 and the second electrode 409 floats against the ground.

Examples of the controller 402 include but not limited to microcontroller, system on chip (SOC), FPGA, state machines etc. Examples of the modem 403 include but not limited to AM, FM, Pulse (de-) modulators, etc. Examples of generator 401 includes but not limited to oscillator, resonator, PWM etc.

The memory unit 410 is connected to the controller 402 for storing media data and operating instructions. The interface 411 preferably communicates wirelessly with the external device 500. Examples of the memory unit 410 include but not limited to RAM, ROM, EEPROM, flash memory or other memory technologies. Examples of the interface 411 includes but not limited to I/O Ports, electronic switches, opto couplers, Bluetooth, wi-fi and other wireless communication units etc.

The third electrode 101 mirrors alternating charges received from the first electrode 405. The energy convertor 102 changes the alternating charges to DC power. The bi-directional communication unit 104 communicates signals with the modem 403 utilizing the alternating electric field and the biological signals.

Examples of the energy convertor 102 include but not limited to rectifier, Graetz bridge, AC-DC convertor, MOS switches. Examples of the bi-directional communication unit 104 includes but not limited to AM or FM (de) modulators, modem sub-circuits, peak detectors, side-band (de) modulators etc.

The analog I/O unit 105 processes (biological) signals received from the bi-directional communication unit 104. The electro-mechanic coupler 106 is coupled to a fixed structure of a living organism 300. The electro-mechanic coupler 106 enhances the (biological) signal. In a preferred embodiment of the present invention, the analog I/O unit 105 is able to sense, decode, convert and amplify the biological signals.

Further, the electro-mechanical coupler 106 generates mechanical waves utilizing the fixed structure 108 and further the electro-mechanical coupler 106 converts mechanical waves into electrical signals and furthermore communicates the electrical signals containing processed biological signals with the analog I/O unit 105. Further, the electro-mechanic coupler 106 emits and receives alternating charges. The electro-mechanic coupler 106 is explained in detail in conjunction with FIG. 2 of the present invention.

The analog I/O unit 105 processes the electrical signals and communicates the information to the bi-directional communication unit 104. The bi-directional unit 104 communicates the information to the modem 403 over the electric field. Furthermore, the controller 402 processes signals from the modem 403 and utilizing the memory unit 410 for operating instructions.

Further, the controller 402 communicates the operating instructions and media data with the external device 500 using the interface 411. The alternating electric field floats between the living organism 300 and the second electrode 409; further the alternating electric field floats in between the living organism 300 and the first electrode 405. Further, the earth's ground surges alternating charges and further creates level difference required for the energy convertor 102.

Examples of the living organism 300 include but not limited to humans, animals, birds, trees, plants etc. Examples of the biological signals include but not limited to audible, appearance, sensing, protection, environmental information, stimulation, vital, mental and physical state of the living organism 300.

The electronic circuitry of the flexible printed circuit 100 harvests usable electric energy (DC) from the field to operate the electro-mechanic coupler 106, which starts to vibrate in the given frequency (ultrasound) while floating the electric field over the user 300 back to ground.

In an exemplary embodiment as shown in FIG. 1, the flexible printed circuit 100 is implanted in the skin of the head 200 to stimulate nerve cells 203 of the human 300. As cells interact via electric fields (ionization, oscillation etc.), the flexible printed circuit 100 has means to include such signals e.g. for monitoring or manipulation purposes.

Further in another exemplary embodiment, the flexible printed circuit 100 stimulates the nerve cells e.g. of user's ear or brain, which may be helpful for impaired users or as a guide, or in a therapy situations. Also, the electric field of cells (e.g. tumors) may be monitored (polarization, ionization, charges, oscillation, osmosis, mitosis etc.) and communicated through the host 400 into networks for further processing. For exemplary purpose, the present invention stimulates nerve cells of a drug addict to suppress his addiction towards the drug.

In another preferred embodiment of the present invention is to provide the system 10, wherein the flexible printed circuit 100 further includes a light source unit 103 to illuminate upon detecting the biological signals from the living organism 300. The controller 402 commands the light source unit 103 on detecting the change in the electric field strength. Further, the controller 402 may command the light source unit 103 on pre-stored time, and other related commands stored in the memory unit 410.

In an exemplary embodiment of the present invention, the light source unit 103 is a multi-color LED. The memory unit 410 stores instructions for illuminating a specific color of the multi-color LED representing a specific (biological) signal. Further, the controller 402 is coupled to the memory unit 410 to command the multi-color LED to illuminate the specific color corresponding to the specific (biological) signal.

Furthermore, the controller 402 may command the light source unit 103 on receiving commands from the external device 500. The controller 402 may command the light source unit 103 to illuminate a specific color LED for different categories of message such as pink for email, red for alert, blue for reminder etc.

In another exemplary embodiment of the present invention, the light source unit 103 is equipped with light emitting elements (e.g. LED, OLED, Laser, etc.) to emit light on commands from the controller 402, which may shine through the user's skin (dermis) for signaling or cosmetically purposes.

Invisible light sources may activate fluorescent zones via UV, (marks fungus, insect bites, also kills germs) or warm up tissue (via IR). The reflection of the light may be measured by the inventions sub circuitry, e.g. to measure blood (pulse, particles, etc.) or other body liquids or juices e.g. inside plants, or e.g. UVA radiation.

The liquids may further be seen as dielectric (impedances) or electrolytes (e.g. Voltage elements). Liquid's amount, consistence, movements or oscillation may have an impact in the applied electric field, which may be measured (or influenced) by the invention related flexible printed circuits and/or communicated and/or interpreted by the host and/or interfaced devices or networks.

In another preferred embodiment of the present invention, wherein the analog I/O unit 105 further stimulates nerve cells 203 of the living organism 300 on receiving instructions from the controller 402. Further, the analog I/O unit 105 monitors the nerve cells 203 and communicates the information to the controller 402 through the bi-directional communication unit 104.

In another preferred embodiment of the present invention is to provide a level shifter 404 for creating controllable levels of modulated frequencies. Examples of the level shifter 404 include but not limited to a resonator, cascade, booster, transformer etc. Examples of mechanical waves include but not limited to ultrasound waves, shocks, audible sounds, contraction of organic material of the living organisms 300.

In another preferred embodiment of the present invention, the memory unit 410 further stores a unique identification ID for each flexible printed circuit implanted. The modem 403 transmits the unique identification ID to activate the analog I/O 105 unit via the bi-directional communication unit 104. The controller process 402 the unique identification ID to first identify the presence and then location of flexible printed circuit 100, and further assist in transmitting and receiving information of the flexible printed circuit 100.

The bi-directional communication unit 104 transmits the processed unique ID from the analog I/O 105 to the modem 403. The controller 402 matches the unique ID stored in the memory unit 410 with the processed unique ID received from the modem 403 via the bi-directional communication unit 104. The controller 402 then selects the related information from the flexible printed circuit 100 and transmits the information to the external device 500 via the interface 411.

The controller 402 calculates the distance vector from the selected flexible printed circuit and identifies location based upon the electric field level absorbed from each flexible printed circuit. The controller 402 further detects changes in the distance e.g. when limbs are moving and such changes are interpretable as gestures to operate the flexible printed circuits.

Figure 2:
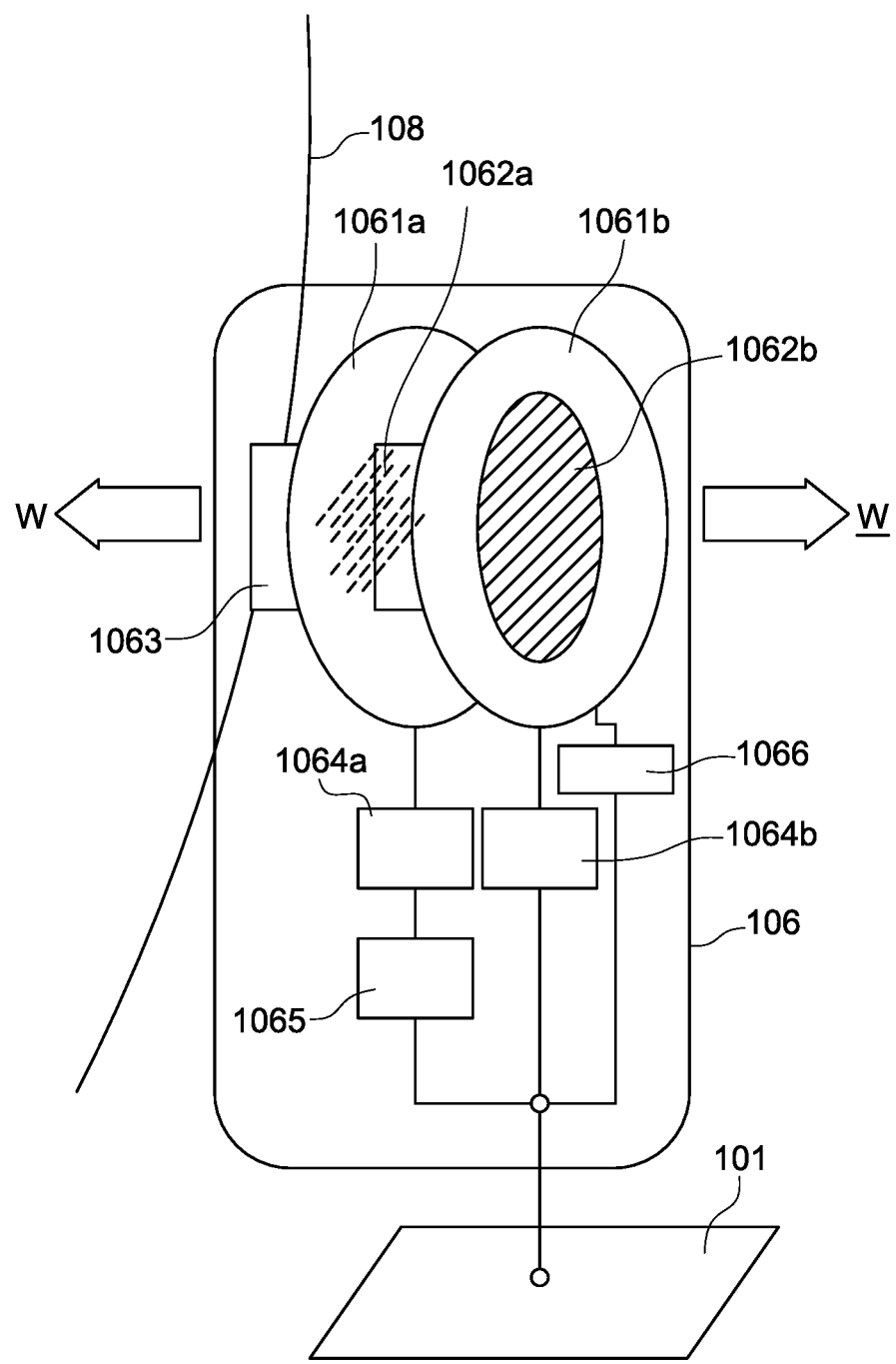
FIG. 2 illustrates a block diagram of an electro-mechanic coupler in accordance with a preferred embodiment of the present invention.

FIG. 2 illustrates a block diagram of an electro-mechanic coupler 106 in accordance with a preferred embodiment of the present invention. The electro-mechanic coupler 106 includes a first conductive membrane 1061*a*, a second conductive membrane 1061*b*, a piezo material 1062, a mechanical acoustic coupler 1063, a first piezo driver 1064*a*, a second piezo driver 1064*b*, a digital frequency modulator 1065 and a biological signal modulator 1066.

The mechanical acoustic coupler 1063 is attached to the fixed structure of living organism. The first conductive membrane 1061*a* is attached to the mechanical acoustic coupler 1063 of living organism (300, shown in FIG. 1) and the second conductive membrane 1061*b* is connected to the first conductive membrane 1061*a* to emit electric field over its surface.

Further, the second conductive membrane 1061*b* is coupled to the mechanical acoustic coupler 1063. Examples of the first conductive membrane 1061*a* and the second conductive membrane 1061*b* include but not limited to conductive foil, thin metal, carbon, graphene, conductive coated flexible surface.

The piezo material 1062*a* is attached to the first conductive membrane 1061*a* and the piezo material 1062*b* is attached to the second conductive membrane 1061*b*. The piezo material 1062*a*, 1062*b* generates mechanical waves. Examples of the piezo and electric field coupler 1062 include but not limited to crystals, quartz, salts, any other material that bends or vibrates under electric influence.

The mechanical acoustic coupler 1063 combines the generated mechanical waves from the first conductive membrane 1061*a* and the second conductive membrane 1061*b*. Further, the mechanical acoustic coupler 1063 filters high frequencies and conducts the resulting beat pattern to the fixed structure 108.

Further, the electro-mechanic coupler 106 includes a mechanical acoustic coupler 1063 for combining the frequencies from the first conductive membrane 1061*a* and the second conductive membrane 1061*b*. Further, the mechanical acoustic coupler 1063 filters high frequency and passes lower frequency to the fixed structure 108.

Further, the first piezo driver 1064*a* operates the first conductive membrane piezo combination 1061*a*/1062*d* and further receives power from the generator via the energy converter 102. Further, the second piezo driver 1064*b* operates the second conductive membrane piezo combination 1061*b*/1062*b* and further receives power from the generator via the energy converter 102.

Further, the digital frequency modulator 1065 modulates the biological signal. The digital frequency modulator 1065 enables the second conductive membrane 1061*b* to resonate and for creating beat patterns. The biological signal modulator 1066 receives biological signal from the first conductive membrane 1061*a*, the biological signal modulator 1066 modulates into e-field received from the host (400, shown in FIG. 1).

Examples of the first piezo driver 1064*a* and the second piezo driver 1064*b* include but not limited to MOSFET, transistors, operational amplifier etc. Examples of the mechanical acoustic coupler 1063 include but not limited to plastic, rubber, artificial bone etc. In an exemplary embodiment of the present invention, after the flexible printed circuit (100 shown in FIG. 1) is implanted in the skin, the tiny wound heals quicker with the mixture of electric field and ultrasound.

The first conductive membrane 1061*a* is connected reverse i.e. 180 degree phase shift to the second conductive membrane 1061*b*. The piezo material is also attached in reverse direction on the first conductive membrane 1061*a* and the second conductive membrane 1061*b*.

When activated, the resulting frequency amplitude (mixture of frequencies from the first membrane and the second membrane) is zero. As the alternating electric field may transport data, such is sent from the host 400 via field modulation (e.g. audio, voice, sounds, signals, vibrations etc.) and received from the flexible printed circuit 100, where it is converted into frequency modulation of the first conductive membrane 1061*a*. The first conductive membrane 1061*a*, the second conductive membrane 1061*b*, the piezo material 1062*a*, 1062*b* hereinafter are described as piezo elements.

As known from the physics, two slightly different and/or counter phased frequencies create a third frequency: a so called "beat pattern" with strong amplitude. The beat pattern passes a mechanical acoustic coupler 1063, which also acts as a low pass filter, e.g. attached to the user's skull. The user gets an "inner" audio experience, while other persons nearby can't hear the transmitted media information, until they come in very close contact with the user, e.g. during kissing.

In an exemplary embodiment of the present invention, the piezo elements may also receive audio signals (similar to microphones) e.g. through the user's ear, or may measure shocks applied to the skull (e.g. fighting boxers, hockey or football players, athletes, drivers, soldiers etc.) The audio signals are transmitted to the host for further processing. Further in another exemplary embodiment of the present inventions, the flexible printed circuit is attached to a tree trunk. The user is able to hear a message by "hugging" the tree, e.g. in an educational situation.

Example of the fixed structure 108 includes but not limited to bone, muscles, organs, fibers, tendon etc for human, and animals; trunks, branches, roots etc for plants. In an exemplary embodiment of the present invention, the fixed support 108 is a bone. The electro-mechanic coupler 106 is attached to the bone 108.

The size of the flexible printed circuit may vary from cm up to nanometers, usable e.g. as "nanobots" inside organic tissue, brain, guts, tumors etc. Such implants may use piezo or other mechanical oscillating elements (e.g. carbon nano tubes) as a kind of motor to reach specific positions inside the organic tissue under the control of the host 400 and/or interfaced devices or networks (powered from the energy convertor 102).

In an exemplary embodiment with reference to FIG. 1 and FIG. 2, the flexible printed circuit (100 shown in FIG. 1) is implanted near the ear (201 shown in FIG. 1) to enhance the hearing experience of a human (300 shown in FIG. 1). The host (400 shown in FIG. 1) powers the flexible printed circuit (100 shown in FIG. 1). The flexible printed circuit (100 shown in FIG. 1) enables the user to hear amplified audio signals over his skull, which acts as a resonator.

The amplified audio signals are processed from the host 400 and transferred to the flexible printed circuit 100. The audio signals are then changed into resonance frequency by the first piezo driver 1064*a*, and the second piezo drivers 1064*b* and connected to the first conductive membrane 1061*a* and the second conductive membrane 1061*b* respectively, in opposite phases (W-W).

The resonance frequency is ultra sound, and the differences between both drivers 1064*a* and 1064*b* create a beat pattern. The mechanical acoustic coupler 1063 suppresses the ultra sound and leads a filtered beat pattern as audio signal to the skull, where the user gets a hearing experience. The mechanical acoustic coupler 1063 is mechanically coupled with the user's skull.

Further in exemplary preferred embodiment of the present invention, an athlete has multiple flexible printed circuits implanted under the skin. The external device sends signals to the flexible printed circuit implanted under the skin of the knee of an athlete to stimulate the movement ability and reflexes. The external device sends signals to controller via the interface.

The controller then processes the signal to select the flexible printed circuit via the allotted unique ID. The controller identifies the accurate flexible printed circuit implanted on the knee by matching the unique ID processed by the analog I/O of the same flexible printed circuit with the unique ID stored in the memory unit. The flexible printed circuit enhances the signal transfers between the nerve system.

Similarly, the above process is followed for enhancing features of living organism like wound healing, hearing, moods, learning, acting, communication, and feelings. It would be readily apparent to those skilled in the art that various features may be enhanced using above procedure without deviating from the scope of the present invention. The present invention offers various advantages such as the following:

1) Integrated Wound Healing—The present invention is able to heal wounds better and faster by providing a combination of ultrasound and electric field waves once the implant is brought into the skin and operating, its ultrasound and electric fields support the healing of the necessary small dermal cut.

2) Audio (Stereo) Implant—Two implants are brought under the skin near a user's ears, bone conductive to the scull. The host transfers the inaudible audio received either from the memory unit or from the external device to the flexible printed circuit. The implant is used for various purposes such as entertainment or education. The implant let the user to hear what others cannot and still reacts to the signals from the environment.

3) Information on Demand—A user, equipped with the invention related implants, may come temporary close to a host, e.g. when operating machines or vehicles, or approaching zones or objects in a specific situation. Information may be passed to the user depending on the situation. The user may also demand such information either as an act of will, or during an activity (e.g. to get specific operating instructions).

4) Interpretation of Gestures—If a user moves his limbs near an implant, the applied electric field may be either bridged or absorbed by his limbs (or other moving body parts), which changes the level of the electric field, received by the implant(s) and communicated to the host. The changes may be interpreted as gestures and used to operate external devices or give instructions to the controller.

5) Nerve Stimulation—Implants may stimulate nerves of the user e.g. to support emotions, dreams, wellness, relaxation, or healing (suppress anxiety or depression). Users with implants may share emotions over distance or networks (e.g. Internet).

6) Monitoring cell activities—As human (or animal) skin reacts on emotions and/or environmental influence, this may be monitored and communicated by the invention related implants, as well as fast growing or oscillating cell clusters (e.g. heart [beating], lungs, but also tumors). In special applications, as implants are flexible, they may also have skin contact from outside e.g. as patches or in underwear. Implemented in e.g. bras, Implants can detect breast cancer in early stages, which improves healing chances.

7) Monitoring plants—Like all living organisms, plants communicate at an electrochemical base, which is also related to electric fields. It is possible to manipulate such communication by applying certain pattern of electric fields, utilizing the invention related implants (attached to plants). It is known that plants react on stimuli like music or special care. A special aspect is covered in the field of bionic, where the invention related implants may be used to monitor or support the interaction between humans and nature.

8) Communicating—Among others (U.A), the invention related implants may emit and receive acoustic waves, while the host unit is connected to communication devices (e.g. SmartPhones). Therefore they may create efficient feedback, e.g. for hearing impaired or for listeners (e.g. in an audience, lecture, or disturbed environment). It is also possible, that a user comes temporarily in the reach of a host to receive and comment location based information.

9) Human Computer—The invention related implants may turn a human into a computer himself, also known as Cyborg. The implants may transfer and receive commands, e.g. to control prostheses or guide blind or other impaired people. First responders, teachers, soldiers etc. may get "hands-free" information or instructions of situations. Action may be monitored for evidence e.g. from pilots, surgeons, babysitters, police, guardians etc. Implants may sense attacks, which invokes alerts. They may also analyze or create (or improve) reflexes, or may help to fight addiction.

In a special variation, miniaturized implants may move inside the body (.e.g. in brain, internal organs, vessels etc.), while their position may be monitored and controlled by the host.

Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

The invention claimed is:

1. A system for enhancing features of a living organism and further communicating the enhancing features with an external device, the system comprising:
   one or more flexible printed circuits implanted under a skin of the living organism; and
   a host placed in proximity of the living organism for powering the flexible printed circuit implant, the living organism generates and receives biological signals, the host comprising:
      a controller for generating commands;
      a generator for generating variable frequency;
      a modem for modulating the generated variable frequency and demodulating a modulated alternating frequency;
      a first electrode for emitting alternating charges with variable frequency, further the first electrode coupled with the living organism;
      a memory unit connected to the controller for storing media data and operating instructions;
      a second electrode floating against a ground; and
      an interface wirelessly communicating with the external device;
   wherein each of the flexible printed circuit comprising:
      a third electrode mirrors alternating charges received from the first electrode;
      an energy converter for changing the alternating charges to DC power;
      a bi-directional communication unit to communicate signals with the modem utilizing the alternating charges and the biological signals;
      an analog I/O unit processes the biological signals received from the bi-directional communication unit; and
      an electro-mechanic coupler coupled to the fixed structure of a living organism, further the electro-mechanic coupler bi-directionally enhances the generated and the received biological signals, further the electro-mechanic coupler generates mechanical waves utilizing the fixed structure and further converts mechanical waves into electrical signals and furthermore communicates the electrical signals containing the processed biological signals with the analog I/O unit, further the electro-mechanic coupler emits and receives alternating charges;
   wherein the analog I/O unit processes the electrical signals and communicates an information to the bi-directional communication unit, wherein the bi-directional unit communicates the information to the modem over the electric field, further wherein the controller processes signals from the modem and utilizing the memory unit for operating instructions and further the controller communicates the operating instructions and media data with the external device using the interface.

2. The system according to claim 1 wherein the electro-mechanic coupler comprising:
   a mechanical acoustic coupler attached to the fixed structure of the living organism;
   a first conductive membrane attached to the mechanical acoustic coupler;

a second conductive membrane connected to the first conductive membrane to emit the electric field over a surface, further the second conductive membrane couples to the mechanical acoustic coupler;

a piezo material attached to the first conductive membrane and the second conductive membrane for generating mechanical waves, wherein the mechanical acoustic coupler combines the generated mechanical waves from the first conductive membrane and the second conductive membrane, further the mechanical acoustic coupler filters high frequencies and conducts resulting beat patterns to the fixed structure;

a first piezo driver operates the first conductive membrane and further receives the DC power from the generator via the energy converter;

a second piezo driver operates the second conductive membrane and further receives the DC power from the generator via the energy converter;

a digital frequency modulator for modulating the frequency of the second membrane with the biological signal; and a biological signal modulator to receive the biological signals from the second conductive membrane, further the biological signal modulator modulates the biological signal into e-field received from the host.

3. The system according to claim 1 wherein the flexible printed circuit further comprising a light source to illuminate through the skin of the living organism on receiving commands from the controller.

4. The system according to claim 1 wherein the analog I/O unit stimulates nerve cells of the living organisms on receiving commands from the controller.

5. The system according to claim 1 wherein the host further comprising a level shifter for creating controllable levels of modulated frequencies.

6. The system according to claim 3 wherein the controller commands the light source unit to illuminate upon detecting the biological signals from the living organism.

7. The system according to claim 6 wherein the light source unit is a multi-color LED, wherein the memory unit stores instructions for illuminating a specific color of the multi-color LED representing a specific biological signal; and the controller coupled to the memory unit to command the multi-color LED to illuminate the specific color corresponding to the specific biological signal.

8. The system according to claim 4 wherein the analog I/O unit monitors nerve cells, further the analog I/O input unit communicates an information to the controller through the bi-directional communication unit.

9. The system according to claim 1 wherein the mechanical waves is at least one of ultrasound waves; shocks; audible sounds; contraction of organic material of the living organism.

10. The system according to claim 9 wherein the flexible printed circuit releases electrical field and ultra sound waves to heal wounds or tissues of the living organisms.

11. The system according to claim 10 wherein the memory unit further stores a unique identification ID for each of the flexible printed circuit implanted; wherein the modem transmits the unique identification ID to activate the analog I/O unit via the bi-directional communication unit; wherein the controller process the unique identification ID to identify the location of each of the flexible printed circuit, and further assist in transmitting and receiving information of the one or more flexible printed circuits.

12. The system according to claim 1 wherein the flexible printed circuit is implanted in objects attached to the living organism.

* * * * *